United States Patent [19]

Brennan

[11] 4,117,227

[45] Sep. 26, 1978

[54] PRODUCTION OF N-(SUBSTITUTED) MORPHOLINE

[75] Inventor: Michael E. Brennan, Austin, Tex.

[73] Assignee: Texaco Development Corp., New York, N.Y.

[21] Appl. No.: 583,015

[22] Filed: Jun. 2, 1975

[51] Int. Cl.$^2$ ............................................. C07D 295/02
[52] U.S. Cl. ...................................... 544/170; 544/87; 544/178; 544/404
[58] Field of Search ........................... 260/247, 247.7; 544/170, 178

[56] References Cited

U.S. PATENT DOCUMENTS

| 615,488 | 12/1898 | Knorr | 260/247 |
|---|---|---|---|
| 3,098,072 | 7/1963 | Cherbuliez et al. | 260/247 |
| 3,641,022 | 2/1972 | Chisholm et al. | 260/247 |
| 3,649,627 | 3/1972 | Fuerst et al. | 260/247 |
| 3,654,271 | 4/1972 | Lamendin et al. | 260/247 |

FOREIGN PATENT DOCUMENTS 259,080  8/1963  Australia .................. 260/247

OTHER PUBLICATIONS

Akagi et al., Chem. Abst., vol. 79, item 146530, (1973).

*Primary Examiner*—Henry R. Jiles
*Assistant Examiner*—R. W. Ramsuer
*Attorney, Agent, or Firm*—Carl G. Ries; Thomas H. Whaley; James L. Bailey

[57] ABSTRACT

An improved process is disclosed for selectively producing an N-(substituted) morpholine compound from the corresponding N-(substituted) diethanolamine compound. The improved process includes contacting the N-(substituted) diethanolamine compound with a catalytically effective amount of a silica-alumina or certain phosphorus-containing substances at temperatures of from about 190° C to about 260° C under a pressure sufficient to maintain the mixture substantially in liquid phase and recovering from the reaction mixture the formed N-(substituted) morpholine.

According to a preferred embodiment, triethanolamine is heated in the presence of a catalytically effective amount of a silica-alumina catalyst having an aluminum content of from about 5 to about 50 wt. % at temperatures of from about 240° C to about 260° C in liquid phase to selectively produce the corresponding N-(hydroxyethyl)morpholine (HEM).

2 Claims, No Drawings

PRODUCTION OF N-(SUBSTITUTED) MORPHOLINE

BACKGROUND OF THE INVENTION

1. Field of the Invention

The instant invention generally relates to an improved process for producing N-(substituted) morpholine compounds from the corresponding N-(substituted) diethanolamine compound, and, more particularly, to an improved liquid phase process for selectively producing N-alkyl morpholine or N-(hydroxyalkyl)morpholine compounds in the presence of certain specific catalytically effective substances.

2. Prior Art

N-alkyl morpholine compounds are well known polyurethane catalysts. N-(hydroxyalkyl)morpholine compounds are used, for example as a base in pharmaceutical applications, a catalyst for polymerizing vicinal epoxides, a polymer modifier and stabilizer, a textile phosphorescent brightner, i.e. dye accepter and as a starting product for producing bis-(morpholino-N-alkyl) ether compounds which have well known utility as polyurethane catalysts.

N-alkyl morpholines are generally prepared by reaction of an alkanol with morpholine. N-(hydroxyalkyl)-morpholine compounds are generally prepared by reaction of morpholine with an alkylene oxide. Morpholine in turn is prepared by various methods, such as, for example, the reaction of diethylene glycol and ammonia over a nickel catalyst at high temperatures and pressures. The disadvantages of such stepwise processes for the preparation of N-(substituted) morpholine compound is readily apparent.

Another known method for preparation of N-alkyl morpholine involves the cyclic dehydration of a corresponding N-(substituted) diethanolamine with stoichiometric amounts of concentrated acid such as hydrochloric, sulfuric and the like with a subsequent neutralization and salt recovery step. A known method for producing N-(2-hydroxyethyl)morpholine from triethanolamine is disclosed in T. Ishiguro, E. Kitamura u. H. Ogawa, J. Pharm. Soc. Japan 75, 1367 (1955); C. A. 50 10106$^c$ (1956). The process involves initially forming a triethanolamine hydrochloride with stoichiometric amounts of acid. The above process involve caustic neutralization with attendant problems.

Another method disclosed for production of N-alkyl substituted morpholine involves the vapor phase cyclic dehydration of a corresponding N-alkyl diethanolamine at 375° C. to 400° C. in the presence of silica-alumina. For example, see I. Ishiguro, E. Kitamura u. H. Matsumura, J. Pharm. Soc. Japan 74, 1162 (1954); C. A. 49, 14767$^g$ (1955). This method suffers from the attendant problem of vapor phase synthesis with low yields and extensive by-product formation. Further, it has been disclosed that amino alcohols such as, for example, di-(2-hydroxypropyl)amine form the corresponding bis-phosphoric acid monoester in the presence of phosphoric acid. See for example U.S. Pat. No. 3,098,072.

It has also been disclosed that N-alkyl morpholines wherein the alkyl moiety contains from 8 to 18 carbon atoms can be produced in liquid phase over an activated alumina catalyst at temperatures that avoid vaporization and decomposition of reagents and products. See for example U.S. Pat. No. 3,641,022.

Unexpectedly, it has been discovered that N-(substituted) morpholine compounds and specifically N-alkyl morpholines and N-(hydroxyalkyl)morpholines can be selectively produced in a single step in liquid phase by use of certain specific catalytically effective substances which are readily available and easily obtained. The selectivity of the instant process to N-(hydroxyalkyl)morpholine compounds is particularly surprising in light of the fact that it has been disclosed that, for example, triethanolamine in the presence of hydrochloric acid yields a myriad of products including the dimorpholinodiethyl ether. In contrast, when using triethanolamine in accordance with the instant process, selective high yield of the N-(2-hydroxyethyl)morpholine compound is produced.

SUMMARY OF THE INVENTION

According to the broad aspect of the instant invention, an N-(substituted) morpholine compound is selectively produced directly from the corresponding N-(substituted) diethanolamine compound, by contacting the N-(substituted) diethanolamine compound with a catalytically effective amount of a silica-alumina or certain phosphorus-containing substances at temperatures of from about 190° C. to about 260° C. under a pressure sufficient to maintain the mixture substantially in liquid phase and recovering from the reaction mixture the formed N-(substituted) morpholine. The N-(substituted) diethanolamine compounds useful in practicing the instant invention can be depicted by the formula:

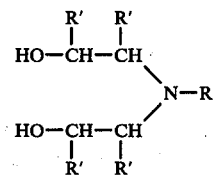

wherein R is an alkyl radical having from 1 to about 8 carbon atoms or a hydroxyalkyl radical having from 1 to about 10 carbon atoms and each R′, independently, is hydrogen or a lower alkyl radical.

According to a preferred embodiment, triethanolamine is heated in the presence of a catalytically effective amount of a silica-alumina catalyst having an aluminum content of from about 5 to about 50 wt.% at temperatures of from about 200° C. to about 260° C. in liquid phase to selectively produce the corresponding N-(2-hydroxyethyl)morpholine (HEM).

DESCRIPTION OF THE PREFERRED EMBODIMENTS

According to a preferred embodiment N-(hydroxyalkyl)diethanolamine compound undergoes a single intramolecular cyclic dehydration reaction at an elevated temperature in the presence of a silica-alumina catalyst, to selectively form the corresponding N-(hydroxyalkyl)morpholine compound.

In a greatly preferred embodiment, triethanolamine is charged into a stirred autoclave with from about 10 wt.% to about 20 wt.% of a silica-alumina containing from about 10 wt.% to about 40 wt.% alumina and having a surface area of from about 50 m²/g to about 700 m²/g. The charged autoclave is then padded with nitrogen and heated to a temperature of from about 190° C. to about 200° C. The autoclave is then gradually heated to temperatures of from about 220° C. to about 250° C. over a 4 to 6 hour period while the reaction pressure is maintained at about 50 psig. The contents of the autoclave are then recovered and the product separated by conventional means such as fractional distillation.

Surprisingly, even at elevated temperatures, only insubstantial amounts of N,N',2,2'-dimorpholinodiethyl ether is formed. Thus, the process is particularly selective to production of N-(2-hydroxyethyl)morpholine.

The N-(substituted) morpholines that can be produced in accordance with the instant invention can be depicted by the general formula:

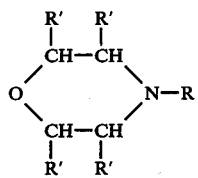

wherein R and R' correspond to the like moieties of the N-(substituted) diethanolamine starting reactant.

The N-(substituted) diethanolamines which are useful in the practice of this invention are those having the formula

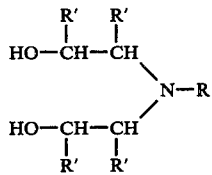

wherein R is an alkyl radical of from 1 to about 10 carbon atoms or an hydroxyalkyl of from 1 to about 8 carbon atoms, and each R', independently, is hydrogen or lower alkyl of from 1 to about 4 carbon atoms. Illustrative dialkanolamines are N-methyldiethanolamine, N-methyl-diisopropanolamine, triethanolamine, N-(3-hydroxypropyl)diethanolamine, triisopropanolamine, and the like. Preferred are the dialkanolamines of the above formula wherein R is an hydroxyalkyl of from about 2 to about 4 carbon atoms and each R', is independently, hydrogen or a methyl radical. Especially preferred is triethanolamine.

The catalysts which are useful in practicing the process of this invention include silica-aluminas, and certain phosphorus-containing substances. The silica-aluminas which are effective as catalysts include those having an alumina content of from about 5 to about 50 wt.% alumina and preferably from about 10 to about 40 wt.% alumina. While silica or alumina utilized alone have proven to be poor catalysts for the process of this invention, the silica-aluminas as herein described affect the cyclical dehydration of the N-(substituted) diethanolamines in high yields and with high selectivity to the desired product.

While most any silica-alumina with an alumina content within the above-mentioned range is effective as a catalyst in the process of this invention, particularly desirable are silica-aluminas with surface areas of from about 50 m²/g to about 700 m²/g.

The silica-alumina can be employed in any well known form such as a fine powder or as a pellet. Pelletized catalysts are particularly suitable for continuous processes in which the catalyst may be employed as a fixed bed. The particular physical form in which the catalyst is employed is not critical in the process of this invention.

Suitable phosphorus-containing substances which can be employed include, for example, acidic metal phosphates, phosphoric acid compounds and their anhydrides, phosphorous acid compounds and anhydrides, alkyl or aryl phosphate esters, alkyl or aryl phosphite esters, alkyl or aryl substituted phosphorous and phosphoric acids, alkali metal monosalts of phosphoric acid, the thioanalogs of the foregoing, and mixtures of any of the above.

More particularly, suitable acidic metal phosphates include metal phosphates such as boron phosphate, ferric phosphate, aluminum phosphate, etc.

Suitable phosphoric acid compounds include aqueous or anhydrous phosphoric acids such as orthophosphoric acid, pyrophosphoric acid, metaphosphoric acid, hypophosphoric acid, and condensed phosphoric acids such as polyphosphoric acids. Accordingly, an example of a suitable phosphorous acid is orthophosphorous acid. Additionally, phosphoric acid-impregnated silicas having from about 10 to about 30 wt.% phosphoric acid may be employed.

In addition, any commercially available mono-, di-, or tri-alkyl or aryl phosphate or phosphite ester can be employed as the catalyst in the invention process. Additionally, bis(phosphates) and secondary phosphate esters such as those disclosed in U.S. Pat. No. 3,869,526 and U.S. Pat. No. 3,869,527, respectively, can be used. Preferably, the lower alkyl esters are employed such as those having from 1 to about 8 carbon atoms per alkyl groups. Preferred aryl esters contain from about 6 to about 20 carbon atoms and may include a phenyl group or alkylsubstituted phenyl group.

Further, suitable alkyl or aryl substituted phosphorous and phosphoric acids which may be employed as a catalyst include alkyl phosphonic acids, aryl phosphonic acids, alkyl phosphinic acids and aryl phosphinic acids. Preferably, such acids include alkyl or aryl groups and have from 1 to about 20 carbon atoms in each aryl or alkyl group.

Specific examples of alkyl and aryl substituted phosphorous and phosphoric acids that may be used in accordance with the invention are phenylphosphinic acid, ethylphosphonic acid, phenylphosphonic acid, naphthaphosphonic acid, and methylphosphinic acid. Examples of the alkyl and aryl substituted phosphorous and phosphoric acid esters are methylphenyl phosphonate, dimethylphenyl phosphonate, methylphenyl phosphinate, ethyl naphthaphosphinate, and propylmethyl phosphonate. When phosphorous acid is employed, it is preferably used in an anhydrous form or in an aqueous solution having from about 10 to about 70 wt.% phosphorous acid. The aqueous phosphorous acid catalyst is miscible with the reactants and is, therefore, a homogeneous catalyst.

The above-mentioned phosphorus-containing substances are not intended to be exhaustive of those that can be employed as a catalyst in the instant inventive process. Those materials set forth are merely intended to be representative of the types of compounds that we have found to be particularly effective. Yet, of the compounds and the types of compounds mentioned, we particularly prefer to emply those that are known to be most reactive such as orthophosphoric acids, polyphosphoric acids, boron phosphate, aluminum phosphate, ferric phosphate, and orthophosphorous acid. Of these, most preferred is orthophosphorous acid.

The amount of catalyst employed in the process of this invention will depend, of course, on the type of catalyst and the particular reactant involved. In batch processes, silica-alumina in an amount of from 1 to about 20 wt.%, based upon the amount of N-(substituted) diethanolamine reactant present, has been found satisfactory, with an amount of from about 5 to about 15 wt.% being preferred. The N-(substituted) diethanolamine is maintained in contact with the catalyst under reaction conditions for a period of time necessary to obtain the desired degree of conversion to products. Generally, a reaction period of from about 1 to about 10 hours will be sufficient. In a continuous reaction process wherein the catalyst is generally employed as a fixed bed, a weight hourly space velocity (WHSV) of from about 0.1 to about 5.0 g/ml catalyst/hr is satisfactory with a space velocity of from about 0.2 to about 2.0 g/ml catalyst/hr being preferred.

The intramolecular condensation reaction of this invention, is carried out in a liquid phase reaction which is conducted at a temperature of from about 190° C. to about 260° C., and preferably at a temperature of from about 200° C. to about 250° C. The exact temperature range is somewhat empirical and will depend upon the particular reactants employed and the desired conversion levels. Temperatures above about 250° C. are shown to substantially reduce selectivity.

The pressure at which the reaction is carried out can be at any pressure sufficient to maintain the reactants substantially in the liquid state. Generally, reaction pressures of from about 10 to about 1,000 psig. have been found satisfactory. However, there is no incentive to employ reaction pressures higher than is necessary to maintain the reactants and products substantially in the liquid state. By substantially in the liquid state is meant the following. As has been discussed previously, water is formed as a co-product of the intramolecular dehydration reaction. It has been found advantageous in batch processes to maintain the water content of the reaction system at as low a level as is possible in order to enhance catalytic activity and shift the equilibrium. Therefore, it is desirable to maintain the reaction zone at a pressure such that the water formed in the bimolecular condensation reaction will be removed from the reaction zone as a vapor. It has been found that for typical reactions, wherein the temperature is maintained in the range of from about 190° C. to about 250° C., the preferable reaction zone pressure is from about 10 to about 50 psig.

In practicing the process of this invention a solvent is not required, but may be employed if desired. Whenever a solvent is employed, the solvent should be non-deleterious to the reaction environment and the desired reaction. Examples of suitable solvents include hydrocarbon solvents such as hexane, decane, dodecene, benzene, and the like, and chlorinated aromatic solvents such as chlorobenzene.

The crude reaction product obtained from the process of this invention will comprise the desired morpholine product, heavy materials and unreacted N-(substituted) diethanolamine. For example, in several embodiments of the process of this invention, it has been found that the catalyst may be recovered from the crude reaction mixture and recycled for reuse according to the process of this invention. It is generally preferable to wash the recovered catalyst, for example with methanol and/or water, and dry it prior to recycling it for reuse.

The N-(substituted) morpholine is recovered from the crude reaction mixture by conventional means, for example distillation, extraction, and the like. Similarly, the unreacted N-(substituted) diethanolamine can be recovered and recycled for conversion to the desired product according to the process of this invention.

The process of this invention will now be further illustrated in the following examples which are for the purposes of illustration and should not be considered a limitation on the scope of the invention.

EXAMPLE I

In a one-liter stirred three-neck glass flask was added 0.89 mol triethanolamine (TEA) and 10.3% by weight of Aerocat ® TA silica-alumina catalyst (74.4 wt.% silica, 25.0 wt.% alumina, 0.6 wt.% other oxides, surface area 550-700 m$^2$/g, American Cyanamid Company). The flask was then continuously purged with nitrogen and heated to a temperature of approximately 195° C. The reaction mixture was gradually heated to a temperature of 240° C. over the next 4.33 hours. The reaction pressure was maintained at atmospheric and the water formed during the reaction was collected overhead. Thereafter, the reaction product mixture was recovered and subjected to gas liquid chromatographic analysis. The analysis showed that 47.4 wt. % of the TEA had been converted to products comprising essentially N-(2-hydroxyethyl)morpholine (HEM) and 2,2'-dimorpholinodiethyl ether (DMDEE). The selectivity to HEM was 78.3% and the selectivity to DMDEE was 3.2%.

EXAMPLE II

According to the general procedure of Exmaple I, a 500 ml stirred, 3-necked, round bottom flask was charged with 298.4 g (2.0 moles) triethanolamine and 8.0 g (0.029 moles) aqueous 30% H$_3$PO$_3$. The charged mixture was heated with stirring to about 180° C. Over the next 1¼ hours, the reaction mixture was gradually heated to a temperature of about 245° C. while the reaction temperture was maintained at atmospheric pressure. The water formed during the reaction was collected overhead. The reaction product mixture was recovered and subjected to gas liquid chromatographic analysis. The analysis showed the following in area %: % triethanolamine conversion, 28.6; % selectivity N-(2-hydroxyethyl)morpholine, 41.4; and % selectivity N,N',2,2'-dimorpholinodiethyl ether, 0.4.

EXAMPLE III

A clean, dry, 1-liter, stirred autoclave was charged with a solution of 357.5 g (3.0 moles) N-methyldiethanolamine and 12.0 g (0.0435 moles) 30% aqueous phosphorous acid. The charged reaction mixture was padded with nitrogen and heated with stirring to 300° C. The heated reaction mixture was held at this temperature for 2 hours at a pressure of 900 to 1,375 psig. The recovered reaction product mixture was analyzed by gas liquid chromatograph and showed the following by area %: % N-methyldiethanolamine conversion, 93.2; % selectivity N-methylmorpholine, 27.5; and % selectivity to dimethylpiperazine, 25.3.

EXAMPLE IV

According to the general procedure of Example III, 1.48 moles of triethanolamine was contacted with 10.0% by weight of Aerocat ® TA silica-alumina catalyst at a temperature of 260° C. for a period of 4.0 hours.

The autoclave pressure was maintained at 380 to 465 psig. Gas-liquid chromatographic analysis of the autoclave contents at the end of the reaction period showed that 100 wt.% of the triethanolamine had been converted to products. The selectivity to N-(2-hydroxyethyl)morpholine was 37.9% and the selectivity to N,N',2,2'-dimorpholinodiethyl ether was 4.7%. The remainder of the products were lighter materials and heavier condensation products.

EXAMPLE V

According to the general procedure of Example III, 357.5 (3.0 moles) N-methyldiethanolamine was contacted with 10.0% by weight of Aerocat ® TA silica-alumina catalyst (25.0% $Al_2O_3$) at a temperature of 260° C. for a period of 4.0 hours at a pressure of 122 to about 400 psig. Gas liquid chromatographic analysis of the autoclave contents at the end of the reaction period showed the following result in area %: % N-methyldiethanolamine conversion, 57.2; % selectivity N-methylmorpholine, 19.2; and % selectivity dimethylpiperazine, 7.5.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for producing an N-(substituted) morpholine compound comprising the steps of contacting an alkanolamine of the formula:

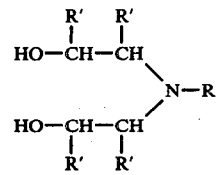

wherein R is an alkyl radical having from 1 to about 8 carbon atoms or a hydroxy alkyl radical having from 1 to about 10 carbon atoms and each R' is, independently, a hydrogen or a lower alkyl radical with a catalytically effective amount of ferric phosphate at a temperature of from about 190° C. to about 260° C. under a pressure sufficient to maintain the mixture substantially in liquid phase; and recovering said N-(substituted) morpholine compound from the reaction mixture.

2. A process for producing an N-(substituted) morpholine compound comprising the steps of contacting an alkanolamine of the formula:

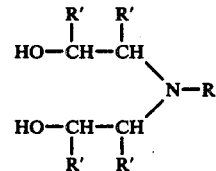

wherein R is an alkyl radical having from 1 to about 8 carbon atoms or a hydroxy alkyl radical having from 1 to about 10 carbon atoms and each R' is, independently, a hydrogen or a lower alkyl radical with a catalytically effective amount of phosphoric acid-impregnated silica having from about 10 to about 30 wt.% phosphoric acid at a temperature of from about 190° C. to about 260° C. under a pressure sufficient to maintain the mixture substantially in liquid phase; and recovering said N-(substituted) morpholine compound from the reaction mixture.

* * * * *